United States Patent [19]

Gray et al.

[11] Patent Number: 5,028,525

[45] Date of Patent: Jul. 2, 1991

[54] METHOD OF PREPARING AND APPLYING SINGLE STRANDED DNA PROBES TO DOUBLE STRANDED TARGET DNAS IN SITU

[75] Inventors: Joe W. Gray, Livermore; Daniel Pinkel, Walnut Creek, both of Calif.

[73] Assignee: Regents of the University of California, Oakland, Calif.

[21] Appl. No.: 543,463

[22] Filed: Jun. 26, 1990

Related U.S. Application Data

[63] Continuation of Ser. No. 934,188, Nov. 24, 1986, abandoned.

[51] Int. Cl.$^5$ .................. G01N 33/566; G01N 33/00; C12Q 1/68
[52] U.S. Cl. .......................................... 435/6; 435/91; 436/501; 436/94
[58] Field of Search ................ 435/6, 259, 91; 935/2, 935/78, 18; 436/501, 94

[56] References Cited

PUBLICATIONS

Schmidt, "Exonuclease Digestion of Chromosomces for in situ Hybridization", *Nucleic Acids Research*, vol. 16 (#21), 1988, p. 10381.
Workman et al., "Necleoprotein Hybridization: A Method . . . ", *Biochemistry*, 1985, 24, 7486-7497.
Old and Primrose, *Studies in Microbiology*, vol. 2, Principles of Gene Manipulation, ed. Carr et al. (University of California Press, Berkeley and Los Angeles, 1981), Chapter 6 Cloning Strategies, pp. 89-90.
James and Leffak, "Replacement Synthesis Labeling of DNA Molecules in vitro Using the Escherichia Coli Exonuclease III/DNA Polymerase I Enzyme Pair", *Anal. Biochem;* 141: 33-37 (1984).
Liao et al., "Cloning of Rat α-Fetoprotein 3'-Terminal Complementary Deoxyribonucleic Acid Sequences and Preparation of Radioactively Labeled Hybridization Probes from Clone Deoxyribonucleic Acid Inserts", *Biochem;* 20: 1646-1652 (1981).
Langer et al., "Enzymatic Synthesis of Biotin-Labeled Polynucleotides: Novel Nucleic Acid Affinity Probes", *PNAS* (U.S.A.), 78 (11): 6633-6637.

*Primary Examiner*—Robert A. Wax
*Assistant Examiner*—Eric Steffe
*Attorney, Agent, or Firm*—Leona L. Lauder; Henry P. Sartorio; Stephen C. Macevicz

[57] ABSTRACT

A method is provided for producing single stranded non-self-complementary nucleic acid probes, and for treating target DNA for use therewith. Probe is constructed by treating DNA with a restriction enzyme and an exonuclease to form template/primers for a DNA polymerase. The digested strand is resynthesized in the presence of labeled nucleoside triphosphate precursor. Labeled single stranded fragments are separated from the resynthesized fragments to form the probe. Target DNA is treated with the same restriction enzyme used to construct the probe, and is treated with an exonuclease before application of the probe. The method significantly increases the efficiency and specificity of hybridization mixtures by increasing effective probe concentration by eliminating self-hybridization between both probe and target DNAs, and by reducing the amount of target DNA available for mismatched hybridizations.

4 Claims, No Drawings

METHOD OF PREPARING AND APPLYING SINGLE STRANDED DNA PROBES TO DOUBLE STRANDED TARGET DNAS IN SITU

The United States Government has rights in this invention pursuant to Contract No. w-7405-ENG-48 between the U.S. Department of Energy and the University of California, for the operation of Lawrence Livermore National Laboratory. This is a continuation of copending application Ser. No. 06/934,188 filed on Nov. 24, 1986, now abandoned.

BACKGROUND OF THE INVENTION

This invention relates generally to nucleic acid hybridization techniques, and more particularly to methods for preparing and applying DNA probes.

Nucleic acid probes have widespread applications in molecular biology, medicine, and biotechnology, e.g., Johnson, "DNA Reassociation and RNA Hybridization of Bacterial Nucleic Acids," *Methods in Microbiology*, Vol. 18, pgs. 33–74 (1985); Petersson et al., "Nucleic Acid Hybridization—An Alternative Tool in Diagnostic Microbiology,"*Immunology Today*, Vol. 6, pgs 268–272 (1985). The probes comprise labeled fragments of single stranded or double stranded DNA or RNA which contain base sequences that are complementary to sequences of interest on target DNAs (or RNAs). Probes are applied to target nucleic acids under conditions which allow the probe to anneal to tne complementary sequence on the target. whenever douole stranded probes or target nucleic acids are involved, they must be converted to single stranded form by heating, or other means, to permit the prooe to anneal to the target. The probe's location on the target, or the location of the target itself, is detected by a label carried by the probe.

Probes are prepared either by cloning and labeling nucleic acids having sequences complementary to those on the target sought to be identified, e.g., via nick-translation, Rigby et al., *J. Mol. Biol.*, Vol. 113, pgs 237–251 (1977), or the like, or by synthesizing labeled oligonucleotides of the appropriate sequence, e.g. Chollet et al., *Nucleic Acids Research*, Vol. 13, pgs. 1529–1541 (1985), or wallace et al., *Nucleic Acids Research*, Vol. 9, pgs 879–894 (1981). In either case probes are prepared independently of any steps for preparing the target nucleic acid for application of the probe. Advantages and disadvantages are associated with each method of constructing probes depending on the particular application contemplated.

One technique for which probe preparation and manner of application is especially important is in situ hybridization. Here target nucleic acids remain in their natural biological settings, e.g., DNA or RNA in chromosomes or nuclei, or in mRNA in cytoplasm. Typically the probes are directed to target sequences which are present in very low copy numbers so that signal-to-noise problems are critical, Angerer et al., "In situ Hybridization to Cellular RNAs," in Setlow and Hollaender, Eds., *Genetic Engineering*, Vol. 7, pgs. 43–65 (1985). As applied to in situ hybridization, current methods of probe construction and application have several drawbacks. whenever double stranded probes are used (or even when single stranded probes are used in some cases) conditions which promote annealing of probe to target also promote annealing of the complementary strands of the probe. The effective concentration of the probe is reduced. If probe concentration is increased to compensate for this effect, background noise increases because of nonspecific and/or mismatched binding of the excess probe.

Current techniques of preparing the target chromosomes or nuclei aim to denature all of the target DNA. whether single stranded or double stranded probe is used, significant mismatcn binding of probe to target can occur because virtually the entire target nucleic acid is denatured and available for hybridization, not just the regions which contain complementary sequences to the probe. Finally, currently used conditions for promoting denaturation are often excessively disruptive to the substrate or biological structure containing the target nucleic acids.

In view of the foregoing it would be desirable to have an alternative procedure for preparing and applying nucleic acid probes which overcame some of the drawbacks associated with current hybridization techniques.

SUMMARY OF THE INVENTION

It is therefore an object of the present invention to provide an alternative method to currently available techniques for preparing and applying non-selfcomplementary single stranded DNA hybridization probes.

Another object of the invention is to improve the signal-to-noise ratios attainable in in situ nybridization by reducing nonspecific and mismatched binding of probe.

Another object of the invention is to provide a method of denaturing double stranded target DNA for application of hybridization probe which minimizes single stranded regions available for hybridization that are noncomplementary to probe sequences.

Additional objects, advantages and novel features of the invention will be set fortn in part in the description wnich follows, and in part will become apparent to those skilled in the art upon examination of the following or may be learned by practice of the invention. Tne objects and advantages of the invention may be realized and attained by means of the instrumentalities and combinations particularly pointed out in the appended claims.

DNA fragments from which probe are to be constructed are treated with a restriction endonuclease which generates a collection of restriction fragments having "sticky" ends, or staggered cuts, characteristic of the endonuclease used. That is, the two fragment ends introduced by a cut each consist of a protruding strand and a recessed strand. The restriction fragments are inserted into vectors which have been engineereo to accept that type of restriction fragment; and the vectors are transfected into host organisms which are grown to increase the number of restriction fragments. Next the vectors are separated from the host organisms, and the restriction fragments are excised and separated from the vectors. On each end of the restriction fragments the recessed strands are digested by an appropriate exonuclease. Digestion is not allowed to go to completion. Tne exonuclease treated restriction fragments are then used as template/primers for DNA polymerase which replaces the digested strand in the presence of a labeled precursor. Examples of enzymes suitable for this process are exonuclease III followed by treatment with the large fragment of DNA polymerase I; or T4 DNA polymerase, which can perform both functions by changes in reaction conditions. After synthesis is completed, the restriction fragments are broken into smaller fragments such tnat the labeled portions of the original restriction fragment remain substantially intact. The smaller fragments are denatured, and the labeled strands are separated from the unlabeled strands to form the hybridization probes.

Before application of the hybridization probe to the target DNA, the target DNA is first treated with the same restriction endonuclease used to excise the probe DNA from the cloning rector. Tnis treatment breaks the target DNA into a collection of restriction fragments having tails at each end characteristic of the restriction endonuclease. Next the target DNA is treated with an exonuclease which removes the recessed strand, thereby exposing single stranded DNA in the vicinity of the cut introduced by the restriction endonuclease. Finally, the hybridization probe is applied to the target DNA, e.g., using standard in situ hybridization protocols, as described more fully below.

An important feature of the invention is treating the cloned probe DNA and the target DNA with the same restriction endonuclease. This ensures tnat the single stranded DNA of the target is complementary to the labeled strand of the probe. Of course many segments of the target in addition to the correct binding sites will be made single stranded because there are many restriction cuts, but there will be much less total single stranded target than would be made by indiscriminant denaturation. In addition, target DNA rendered single stranded in this manner cannot reanneal with itself and thus block access to the probe.

Another important (but not critical) feature of the invention is the selection of a label which permits labeled strands to be separated from unlabeled strands. Preferably precursors are labeled by biotinylation, and the labeled strands are separated from unlabeled strands by affinity chromatograpny.

The present invention addresses problems associated with the hybridization of nucleic acid probes to double stranded target DNAs, particularly in connection with in situ hybridization. The problem of nonspecific binding is mitigated by construction probes which do not have self-complementary base sequences. Thus, effective probe concentration is not reduced by self-hybridization, and lower probe concentrations can be employed which, in turn, result in less nonspecific binding. The problem of mismatched binding of probe to target sequences which are not perfectly complementary is mitigated by minimizing the amount of single stranded target segments that is produced while assuring that the properly homologous binding sites are exposed.

DETAILED DESCRIPTION OF THE PREFERRED EMBODIMENT

The invention is a method for preparing and applying single stranded DNA hybridization probes to double stranded target DNA. Generally the method involves treating both target DNA and probe DNA with the same restriction endonuclease followed by digestion of single strands adjacent to the restriction cuts. Probes are constructed by resynthesizing the digested single strands with labeled nucleotides. The labeled strands are substantially complementary to the undigested single strands of the target DNAs. The double stranded DNA fragments containing the labeled single strands are broken into smaller pieces and denatured. The hybridization probes are obtained by separating the labeled single stranded fragments from the unlabeled fragments.

DNA to be used in the probes is treated with a restriction endonuclease to form restriction fragments having "sticky" ends. That is, it is important that the restriction endonuclease make a staggered cut through the double stranded DNA. Suitable restriction endonuclease include, but are not limited to, Hind III, Bam Hl, Eco Rl, or the like, all of which are commercially available, e.g., Promega Biotec (Madison, Wis.), or Boehringer Mannheim (Indianapolis, Ind.). In selecting a restriction endonuclease it is preferable that the resulting restriction fragments be witnin a size range which allows them to be directly inserted into available cloning vectors. Suitable cloning vectors included plasmids, such as pBR322, and phages, such as lambda phage, various derivatives of both of these being commercially available, e.g., Promega Biotec (Madison, Wis.), and Boehringer Mannheim (Indianapolis, Ind.). Amplified copies of the restriction fragments are isolated using standard techniques, e.g., Maniatis et al., *Molecular Cloning: A Laboratory Manual* (Cold Spring Harbor Laboratory, 1982). Alternatively, for some applications restriction fragments can be obtained from existing libraries. For example, the American Type Culture Collection, Rockville, Md, holds collections of human chromosome-specific libraries of restriction fragments which are available to the public.

Standard procedures are followed in treating the restriction fragments with exonuclease, and in enzymatically re-synthesizing the digested strands in the presence of labeled precursors. In particular the technique disclosed by James and Leffak, *Anal. Biochem.*, Vol. 141, pgs. 33-37 (1984), is followed. Accordingly this reference is incorporated by reference. Briefly, to the restriction fragments about 3 units of exonuclease III are added per microgram of DNA in a solution consisting of 100 mM NaCl, 50 mM Tris-HCl (pH 8.0), 10 mM $MgCl_2$ and 1 mM dithiothreitol, at 37° C. Digestion is terminated by heating the sample to 60° C. for 5-10 minutes. James and Laffak report that these conditions result in the digestion of about 80-200 nucleotides per minute. The actual digestion rate will vary depending on the source and batch of exonuclease III as well as the source of the DNA substrate, e.g., Guo et al., *Nucl. Acids Res.*, Vol. 10 pg. 2065. Some experimentation may be necessary to obtain labeled stands of the desired length. Exonulcease III is available commercially, e.g., Boehringer Mannmheim (Indianapolis, Ind.), or Promega Biotec (Madison, Wis.). Also, T4 polymerase (BRL, Bethesda, Md.) can be used for both the exonuclease and resynthesis steps.

The exonuclease treated restriction fragments serve as primer/templates for a DNA polymerase which re-synthesizes the digested strands in the presence of labeled precursors. The preferred labeled precursor is biotinylated uracil, as a substitute for thymidine. Resynthesis is accomplisned using DNA polymerase I or T4 DNA polymerase following the procedure of Langer et al., *Proc. Nat'l. Acad. Sci.*, Vol. 78, pgs. 6633-6637 (1981) which, in turn, is an adaption of the basic nick translation technique disclosed by Rigby et al., *J. Mol. Biol.*, Vol. 113, pg. 237 (1977), e.g., 1 unit *E. Coli* polymerase I per microgram of DNA is incubated at 37° C. in a solution consisting of 100 mM Nacl, 50 mM Tris-HCl (pH 8.0), 10 mM $MgCl_2$, 1 mM dithiothreitol, and 50 mM KCl. Also included in the solution are appropriate amounts of the triphosphate precursors (one or more of which are labeled), e.g., 50-100 micromolar of each for 20-50 micrograms per milliliter of restriction fragments. Under these conditions resynthesis is completed in about 40-60 minutes.

The labeled restriction fragments are broken into smaller fragments to ensure that the labeled regions on either end of the labeled restriction fragments are separated. (Otherwise, the labeled fragment on one end would be a part of a larger piece of single stranded DNA which contained complementary regions to the labeled fragment on the other end). Such breaking into smaller fragments is accomplished by any number of standard techniques, e.g. sonication, enzymatic treatment, or the like, Maniatis, et al. *Molecular Cloning: A Laboratory Manual* (Cold Spring Harbor Laboratory, 1982).

After the labeled restriction fragments are appropriately broken into smaller pieces, they are denatured and single stranded labeled fragments are separated from unlabeled fragments. The separation can be accomplished in several ways. Whenever the preferred label, biotin, is used the preferred separation means is by way of a standard avidin affinity column, e.g. Bayer and wilchek, "The Use of the Avidin-Biotin Complex as a Tool in Molecular Biology," *Methods of Biochemical Analysis*, Vol 26, pgs. 1-45 (1980); and Manning et al., *Biochemistry*, Vol. 16, pgs. 1364-1370 (1977). Avidin can be covalently coupled to a number of different substrates, such as glass, Sepharose, agarose, and the like, with standard techniques as described in the above references. Accordingly, Manning et al. and Bayer and wilchek, pgs. 9-16, are incorporated by reference. Avidin affinity columns are also available commercially, e.g. Zymed Laboratories, Inc. (South San Francisco, Calif.). The biotinylated probes are removed from the avidin column following the procedure of Chollet and Kawashima, *Nucleic Acid Resources*, Vol. 5 pgs. 1529-1541 (1985). Briefly, for about 1 nmol of DNA, 0.2 ml of avidin-agarose (e.g. Sigma Chemical Co., 50 units per ml.) is washed successively with 2 ml A buffer (1M NaCl, 0.01M sodium phosphate, pH 7.0), 0.5 ml A buffer saturated with biotin at a 2-3 ml/hr flow, 0.6 ml A buffer, 0.6 ml B buffer (2M urea in A buffer) and 1 ml C buffer (6M guanidinium hydrochloride pH 2.5). The column is regenerated by washing with 1 ml A buffer. The reaction mixture containing the labeled fragments is loaded in A buffer at 2-3 ml/hr flow. Components of the reaction mixture other than the biotinylated fragments are washed off the column with 0.6 ml B buffer. The biotinylated fragments are eluted off the support with 0.9 ml C buffer, dialysed against 10 mM thiethylammonium-bicarbonate pH 7.5 and lyophilized.

Alternatives to the above labeling procedure are available. For example, after the DNA to be used in the probes is treated with a restriction endonuclease, the resulting restriction fragments are separated into two portions. The first portion undergoes treatment as described above. That is, it is treated with exonuclease to form template/primers for resynthesizing a labeled strand of DNA. The resulting resynthesized restriction fragments are then broken into smaller pieces, as described above. The label in this case, need not be biotin. For example, a radioactive label can be used. The second portion is also treated with an exonuclease, preferably exonuclease III. However, the reaction is allowed to proceed to completion so that each restriction fragment is converted into two noncomplementary single stranded pieces approximately half the length of the parent strand. These resulting single strands are then covalently linked to DBM paper using standard techniques, e.g. Maniatis et al; *Molecular Cloning: A Laboratory Manual* (Cold Spring Harbor Laboratory, 1982) pgs. 335-339; and Alwine et al., *Methods in Enzymology*, Vol. 68, pgs. 220-242 (Academic Press, New York, 1979). Accordingly, the cited pages of these references are incorporated by reference. The fragments of the first portion are denatured and combined with the DBM paper containing the covalently linked fragments of the second portion. Conditions are adjusted to permit hybridization of the labeled strands to complementary strands covalently linked to the DBM paper. The unlabeled strands from the first portion are washed from the paper (there being no complementary strands for them to hybridize to). After the washing the labeled strands are removed by heating, for example, and are ready for use.

Before application of the probe to the target DNA, the target DNA is treated with the same restriction endonuclease as was used in construction of the probe. After restriction endonuclease treatment the target DNA is treated with an exonuclease, preferably exonuclease III or T4 polymerase. Preferably, the conditions of exonuclease treatment are adjusted so that the lengths of single stranded regions created are substantially the same as the lengths of the probe DNA.

Hybridization of probe to target DNA is carried out using standard procedures, e.g. Gall and Pardue, *Methods in Enzymology*, Vol. 21, pgs. 270-480 (1981); Henderson, *International Review of Cytology*, Vol. 76, pgs. 1-46 (1982); and Angerer et al., in *Genetic Engineering: Principles and Methods*, Setlow and Hollaender, Eds., Vol. 7, pgs. 43-65 (Plenum Press, New York, 1985). Accordingly, these references are incorporated by reference as guides for the use of the invention in in situ hybridization. Briefly, probe prepared in accordance with the invention is combined with several other agents for reducing nonspecific binding, for maintaining the integrity of the biological structure being probed, and the like. The resulting mixture is referred to herein as the hybridization mix.

An important application of the present invention is the treatment of chromosomes with chromosome-specific stains consisting of a heterogeneous mixture of hybridization probes to unique sequence regions of the target chromosomes, as described in copending U.S. patent application Ser. No. 819,314 filed Jan. 16, 1986, and by Pinkel et al., *Proc. Nat'l Acad. Sci.*, Vol. 83, pgs. 2934-2938 (1986). Below, the method of the invention is applied in the chromosome-specific staining of human chromosome 21.

Hind III restriction fragments of human chromosome 21 are available from the National Laboratory Gene Library Project through the American Type Culture Collection, Rockville, Md. Van Dilla et al., "Human Chromosome-Specific DNA Libraries: Construction and Availability," *Biotechnology*, Vol. 4, pgs. 537-552 (1986). Alternately, such fragments can be produced following the disclosures in Van Dilla et al., cited above, or Fuscoe et al., "Contruction of Fifteen Human Chromosome-Specific DNA Libraries from Flow-Purified Chromosomes, " *Nucleic Acids Research*, (1986), which references are incorporated by reference.

Clones from the library having unique sequence inserts are isolated by the method of Benton and Davis, *Science*, Vol. 196, pgs. 180-182 (1977). Briefly, about 1000 recombinant phage are isolated at random from the chromosome 21-specific library. These are transferred to nitrocellulose and probed with nick translated total genomic human DNA.

Of the clones which do not show strong nybridization, approximately 300 are picked which contain apparent unique sequence DNA. After the selected clones are amplified, the chromosome 21 insert in each clone is $^{32}$p labeled and hybridized to Southern blots of human genomic DNA digested with the same enzyme used to construct the chromosome 21 library, i.e., Hind III. Unique sequence containing clones are recognized as those that produce a single band during Southern analysis. Roughly, 100 such clones are selected for the heterogeneous mixture of probe DNA. The unique sequence clones are amplified, the inserts are removed by Hind III digestions, and the inserts are separated from the phage arms by gel electrophoresis. The probe DNA fragments (i.e., the unique sequence inserts) are removed from the gel and treated with exonuclease III as described above, followed by resynthesis in the presence of biotinylated UTP precursor. The resulting double stranded fragments are sonicated so that on an average each fragment receives about 1.5–2.0 breaks. The resulting pieces are denatured and the biotinylated fragments are isolated by avidin affinity chromotography as described above.

Human lymphocyte chromosomes are prepared following Harper et al., *Proc. Natl Acad. Sci.*, Vol. 78, pgs. 4458–4460 (1981). Metaphase and interphase cells are washed 3 times in phosphate buffered saline, fixed in methanol-acetic acid (3:1) and dropped onto cleaned microscope slides. Slides are stored in a nitrogen atmosphere at −20° C.

Slides carrying interphase cells and/or metaphase spreads are removed from the nitrogen treated with RNase (100 micrograms/ml for 1 hour at 37° C.), treated for about 1–16 hours with Hind III at 37° C. (10 units M 10 mM Tris-HCl, 50 mM NaCl, 10 mM MgCl$_2$, and 14 mM dithioenythritol at pH 7.6), treated with exonuclease III as described above, and dehydrated in an etnanol series. They are then treated with proteinase K (60 ng/ml at 37° C. for 7.5 minutes) and dehydrated. The proteinase K concentration is adjusted depending on the cell type and enzyme lot so that almost no phase microscopic image of the chromosomes remains on the dry slide. The hybridization mix consists of (final concentrations) 2×SSC (0.15M NaCl and 0.015M sodium nitrate) 10 percent dextran sulfate, 500 micrograms/ml carrier DNA (sonicated herring sperm DNA), and 2.0 microgram/ml biotin-labeled probe DNA. This mixture is applied to the slides at a density of 3 microliters/cm$^2$ under a glass coverslip and sealed with rubber cement. After overnight incubation at 37° C., the slides are washed at 45° C. (50% formamide-2×SS pH 7, 3 times 3 minutes; followed by 2×SSC pH 7, 5 times 2 minutes) and immersed in BN buffer (0.1M Na bicarbonate, 0.05 percent NP-40, pH 8). The slides are never allowed to dry after this point.

The slides are removed from the BN buffer and blocked for 5 minutes at room temperature with BN buffer containing 5% non-fat dry milk (Carnation) and 0.92% Na Azide (5 microliter/cm$^2$ under plastic coverslips). The coverslips are removed, and excess liquid briefly drained and fluorescein-avidin DCS (3 microgram/ml in BN buffer with 5% milk and 0.02% Na Azide) is applied (5 microliter/ cm$^2$. The same coverslips are replaced and the slides incubated 20 minutes at 37° C. The slides are then washed 3 times for 2 minutes each in BN buffer at 45° C. The intensity of biotin-linked fluorescence is amplified by adding a layer of biotinylated goat anti-avidin antibody (5 microgram/ml in BN buffer with 5% goat serum and 0.02% NaAzide) followed, after washing as above, by another layer of fluorescein-avidin DCS. Fluoresceinavidin DCS, goat antiavidin and goat serum are all available commercially, e.g., Vector Laboratories (Burlingame, Calif.). After washing in BN, a fluorescence antifade solution, p-phenylenediamine (1.5 microliter/cm$^2$ of coverslip) is added before observation. It is important to keep this layer thin for optimum microscopic imaging. This antifade significantly reduced fluorescein fading and allows continuous microscopic observation for up to 5 minutes. The DNA counterstains (DAPI or propidium iodide) are included in the antifade at 0.25–0.5 microgram/ml.

The red-fluorescing DNA-specific dye propidium iodide (PI) is used to allow simultaneous observation of hybridized probe and total DNA. The fluorescein and PI are excited at 450–490 nm (Zeiss filter combination 487709). Increasing the excitation wavelength to 546 nm (Zeiss filter combination 487715) allows observation of the PI only. DAPI, a blue fluorescent DNA-specific stain excited in the ultraviolet (Zeiss filter combination 487701), is used as the counterstain when biotin-labeled and total DNA are observed separately. Metaphase chromosomes 21s are detected by randomly located spots of yellow distributed over the body of the chromosome.

The descriptions of the foregoing emodiments of the invention have been presented for the purpose of illustration and description. They are not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A method of preparing and hybridizing single stranded DNA probes to double stranded target DNA in situ, the method comprising the steps of:

providing restriction fragments having staggered ends, the staggered ends each consisting of a protruding strand and a recessed strams;

digesting a portion of the recessed strand with an exonuclease to form combined templates and primers;

resynthesizing said digested DNA strand along the combined templates and primers with a DNA polymerase in the presence of a labeled nucleoside triphosphate precursor to form labeled resynthesized fragments;

making a sufficient number of double-stranded breaks of the labeled resynthesized fragments so that the labeled regions on opposite ends of each resynthesized fragment are on separate pieces of DNA;

denaturing the broken labeled resynthesized fragments into labeled and unlabeled single strands;

separating the labeled resynthesized strands of the DNA fragments from the unlabeled strands to form the single stranded DNA probe;

treating the double stranded target DNA in situ with the same restriction endonuclease used to generate the restriction fragments;

after treasting with the restriction endonuclease digesting the double stranded target DNA with an exonuclease; and after digesting with the exonuclease, hybridizing the single stranded DNA probe to the double stranded target DNA in situ.

2. The method of claim 1 wherein said labeled nucleoside triphosphate precursor is biotinylated uracil triphosphate and wherein said step of separating includes passing said denatured broken synthesized fragments over an avidin affinity column.

3. The method of claim 1 wherein said step of breaking the labeled resynthesized fragments is accomplished by the use of sonication and/or enzymatic digestion.

4. A method according to claim 1 wherein said single stranded DNA probes are chromosome-specific.

* * * * *